US00PP30055P2

(12) United States Plant Patent
Bedard

(10) Patent No.: US PP30,055 P2
(45) Date of Patent: Jan. 8, 2019

(54) CLIMBING ROSE PLANT NAMED 'WEKVALDAOM'

(50) Latin Name: *Rosa hybrida*
Varietal Denomination: WEKvaldaom

(71) Applicant: Early Morning LLC, Lawrenceburg, IN (US)

(72) Inventor: Christian Bedard, Placentia, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 15/732,477

(22) Filed: Nov. 16, 2017

(51) Int. Cl.
*A01H 5/02* (2018.01)

(52) U.S. Cl.
USPC ..... Plt./115

(58) Field of Classification Search
USPC ..... Plt./115
See application file for complete search history.

(56) References Cited

U.S. PATENT DOCUMENTS

PP17,687 P2 5/2007 Carruth
PP24,728 P3 8/2014 Bedard

*Primary Examiner* — Annette H Para
(74) *Attorney, Agent, or Firm* — McKee, Voorhees & Sease, PLC

(57) ABSTRACT

A new variety of Climbing rose suitable for garden decoration, having flowers of dark red coloration.

1 Drawing Sheet

Classification: The present invention relates to a new *Rosa hybrida* plant.

Variety denomination: The new plant has the varietal denomination 'WEKvaldaom'.

BACKGROUND OF THE INVENTION

This invention relates to a new and distinct variety of Climbing Rose. It has as its seed parent the variety known as 'WEKamrav' (U.S. Plant Pat. No. 17,687) and as its pollen parent the variety known as 'WEKcisfrabo' (U.S. Plant Pat. No. 24,728).

SUMMARY OF THE INVENTION

Among the features which distinguish the new variety from other presently available and commercial rose cultivars known to the inventor are the following combinations of characteristics: its large flower size for the class, its dark red coloration that does not burn under intense sunlight and its excellent color stability throughout the life of the flower. The plant has a spreading climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations.

'WEKvaldaom' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKamrav' by the following combination of characteristics: whereas 'WEKvaldaom' bears medium to large sized (about 8.2 to about 12.1 cm. in diameter) very double flowers (about 25 to 50 petals), 'WEKamrav' bears significantly smaller flowers (about 4.8 to about 7.2 cm. in diameter) with lesser petalage (about 25 to 36 petals).

The new variety may be distinguished from its pollen parent, 'WEKcisfrabo' by the following combination of characteristics: whereas 'WEKvaldaom' bears very double flowers (about 25 to 50 petals), 'WEKcisfrabo' bears double flowers with significantly lesser petalage (about 18 to 28 petals). The new variety is classified as climbing rose with a spreading climbing medium height growing habit with canes about 180 cm. to about 230 cm. in length, whereas the pollen parent is classified as a floribunda rose with a significantly smaller upright moderately spreading growing habit (about 120 to about 180 cm. in height).

COMPARISON WITH THE CLOSEST COMMERCIALLY AVAILABLE CULTIVAR

The closest commercially available cultivar to the new variety is the seed parent 'WEKamrav' (U.S. Plant Pat. No. 17,687).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety sometimes bears its flowers singly, sometimes in clusters of two to four or more per stem. Flowers may be borne in regular rounded clusters on strong somewhat short to long stems (about 18 to about 78 cm.). The cluster ranges from about 16.0 to about 20.0 cm. in diameter. Outdoors, the plant blooms abundantly and nearly continuously during the growing season. The flowers have a slight tea fragrance.

BUD

The peduncle is about 2.4 to about 4.6 cm. in length, of average caliper (about 0.2 to about 0.3 cm. in diameter), and usually erect. It is moderately rough, with few stipitate glands and hairs. Peduncle color is between 146C and 146B often moderately suffused, especially on the side exposed to the sun, with between 183A and 183B.

Before the calyx breaks, the bud is about 1.3 to about 1.6 cm. in diameter at the widest point, about 1.5 to about 2.1 cm. in length, and pointed to somewhat ovoid in shape. The surface of the bud bears between 7 to 10 foliaceous appendages, usually with slender entire foliaceous parts extending beyond the tip of the bud about ¼ or more of its length. Bud color is between 137C and 146A sometimes lightly suffused, especially on the side exposed to the sun, with between 187B and 187A.

The sepals are five per flower, about 2.0 to about 3.1 cm. in length and about 0.8 to about 1.2 cm. in width at the widest point. The outer surface color of the sepal is between 137C and 146A sometimes lightly suffused, especially on the side exposed to the sun, with between 187B and 187A. The outer surface of the sepal is smooth and bears between 0 to 6 foliaceous appendages. The inner surface color of the sepal is near 146C broadly bordered by near 137B. After the sepals open, the inner surface color is sometimes moderately suffused, especially on the area exposed to the sun, with between 187B and 187A. The inner surface of the sepal is covered with fine wooly tomentum; sepal margins are entire and lined with few stipitate glands and many hairs. The sepals are moderately fugacious, usually straight in shape with acute apices.

The receptacle of the flower is of somewhat long length (about 0.7 to about 1.0 cm.) and moderately heavy in caliper (about 0.7 to about 1.1 cm. in diameter). The receptacle is urn-shaped in form. Its surface is smooth with few hairs and with thin fleshy walls. The receptacle color is between 146C and 146D sometimes lightly suffused, especially on the area exposed to the sun, with between 187C and 187B.

As the petals open (after the calyx breaks), the bud is about 2.0 to about 2.4 cm. in diameter at the widest point, about 2.2 to about 2.8 cm. in length, and moderately ovoid to somewhat globular in form. The color of the under surfaces of the newly opened petals is near 187B often heavily suffused, especially on the outermost petals with near 187A. At the point where the petal attaches, there is a small zone of between 150D and 149D. The color of the upper surfaces of the newly opened petals is near 187A. At the point where the petal attaches, there is a moderately small zone of between 154C and 150C.

BLOOM

When fully open, the bloom ranges from about 8.2 to about 12.1 cm. in diameter. Petalage is very double with about 25 to 50 petals and about 5 to 10 petaloids irregularly arranged. When partially open, the bloom form is moderately high centered to cupped, and the petals are somewhat loosely spiraled to cupped with petal edges somewhat reflexed outward. When fully open, the bloom form is more cupped, and the petals are loosely cupped to moderately undulated with petal edges moderately reflexed outward.

PETALS

The substance of the petals is moderately heavy and of somewhat thick thickness, with upper surfaces moderately satiny to somewhat velvety and under surfaces moderately shiny. The petals are about 3.0 to about 5.0 cm. in length and about 2.1 to about 5.4 cm. in width at the widest point. Petal margins are entire to sometimes somewhat dentate, mostly on the outermost petals.

The outer petals are nearly round to somewhat obovate in shape with rounded apices to sometimes somewhat lacerated.

The inner petals are moderately obovate in shape with rounded apices and sometimes slightly notched with one notch.

Petaloids are about 0.8 to about 4.1 cm. in length and about 0.5 to about 2.7 cm. in width at the widest point. Petaloids are irregularly shaped moderately obovate to oblanceolate to somewhat subulate with rounded apices.

NEWLY OPENED FLOWER

The under surface color of the outer, intermediate and inner petals is between 53B and 46A. At the point where the petal attaches, there is a small zone of between 1D and 2D. The upper surface color of the outer, intermediate and inner petals is between 53A and 46A. At the point where the petal attaches, there is a somewhat small zone of between 11A and 13C.

The under and upper surface colors of the petaloids are similar in coloration to the upper and under surfaces of the intermediate and inner petals.

The general tonality of the newly opened flower is between 53A and 46A.

THREE-DAY-OLD FLOWER

The under surface color of the outer, intermediate and inner petals is between 60A and 46A. At the point where the petal attaches, there is a small zone of between 1D and 2D. The upper surface color of the outer, intermediate and inner petals is between 53A and 46A. At the point where the petal attaches, there is a somewhat small zone of between 4C and 3D.

The under and upper surface colors of the petaloids are similar in coloration to the upper and under surfaces of the intermediate and inner petals.

The general tonality of the three-day-old flower is between 53A and 46A.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids. The filaments are moderately of short to long length (about 0.5 to about 1.3 cm.) most with anthers. Filaments are between 4B and 5C in color sometimes lightly suffused with between 53C and 53B. The anthers are of medium size for the class and all open approximately at the same time. Anther color when immature is near 22A on the external part and near 11D on the internal part sometimes moderately suffused with between 53B and 53C. Anther color at maturity is near 164C on the external part and near 200A on the internal part. Pollen is moderately abundant and between 22B and 23C in color.

FEMALE REPRODUCTIVE ORGANS

Pistils vary in number (average about 85). The styles are somewhat uneven, short to average in length (about 0.3 to about 0.8 cm.), average in caliper, and loosely bunched to somewhat separated. Stigma color is between 11B and 10B. Style color is near 150D often lightly suffused with between 53C and 53D. Ovaries are usually all enclosed in the calyx. The ovaries are of small size and between 158B and 158C in color.

Hips are of average to somewhat long length (about 1.5 to about 2.6 cm.), urn-shaped to somewhat rounded in form, and near 31A in color when ripe. The hip surface is smooth with thick fleshy walls.

The seeds are irregularly rounded, smooth in texture, approximately 4 to about 11 per hip, about 0.4 to about 0.8 cm. in diameter at the widest point and between 164C and 165D in color.

FOLIAGE

The compound leaves are usually comprised of three to seven leaflets and are borne abundantly. The five-leaflet leaves are about 8.8 to about 16.4 cm. in length and about 6.7 to about 14.3 cm. in width at the widest point, somewhat leathery to moderately crisp in texture on both sides, and glossy in finish on the upper side and slightly glossy in finish on the under side. The leaves have a pinnate venation pattern. The terminal leaflets are about 5.1 to about 8.5 cm. in length and about 2.8 to about 5.5 cm. in width at the widest point, shaped ovate to moderately oval with acute apices and rounded bases. Their margins are usually simply serrate.

The upper surface color of the mature leaf is between 139A and 137A. The under surface color of the mature leaf is between 147B and 137C. The under and upper colors of the leaf veins on the mature leaf are similar in coloration to the upper and under surfaces colors of the mature leaf. The upper surface color of the young leaf is near 137B, often heavily suffused with between 187A and 187B. The under surface color of the young leaf is between 138B and 139C, often heavily suffused with between 187A and 187B. The under and upper colors of the leaf veins on the young leaf are similar in coloration to the upper and under surfaces colors of the young leaf.

The rachis is about 3.7 to about 6.9 cm. in length and about 0.1 to about 0.2 cm in width at the widest point and somewhat rough. The upper side is deeply grooved with few hairs and stipitate glands on the edges of the grooves. The under side of the rachis is somewhat rough with few hairs and small prickles. The rachis color is near 146C on the under side and near 137B on the upper side, often heavily suffused on the young leaves with between 187A and 187B.

The stipules are about 1.2 to about 2.5 cm. in length and somewhat wide (about 0.4 to about 0.9 cm.) with medium to somewhat short straight points that usually turn out at an angle of more than 45 degrees and often recurve toward the stem. The under and upper surface color of the stipule is between 137A and 137B, often heavily suffused on the young leaves with between 187A and 187B. The upper and under surfaces of the stipules are smooth in texture.

The petiole is average in caliper and somewhat rough. The upper side is deeply grooved with few hairs and stipitate glands on the edges of the grooves. The under side of the petiole is somewhat rough with few hairs and small prickles. The petiole is about 0.7 to about 1.5 cm. in length and about 0.1 to about 0.2 cm in width at the widest point. The petiole color is near 146C on the under side and near 137B on the upper side, often heavily suffused on the young leaves with between 187A and 187B.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has a spreading climbing medium height growing habit with canes about 180 cm. to about 230 cm. in length with very full branching. It displays moderately vigorous growth and the canes are of medium to somewhat heavy caliper for the class (about 1.7 to about 3.1 cm. in diameter at the widest point).

The color of the major stems is between 146B and 147B. The major stems are rough in texture and they bear some large prickles that are about 0.7 to about 1.0 cm. in length. The large prickles are angled moderately downward with a long broad oval base; prickle color is near 177B often heavily suffused with between 201B and 201C. The major stem bears many small prickles of similar shape and coloration.

The color of the branches is between 146B and 146A. The branches are rough in texture and they bear some large prickles which are of similar size and shape to the large prickles on the major stems; prickle color is between 152C and 146C. The branches bear few small prickles of similar shape and coloration.

The color of the new shoots is between 146B and 146A often moderately suffused with between 187B and 187A. The new shoots are rough in texture and they bear some large prickles which are of similar size and shape to the large prickles on the major stems; prickle color is between 152B and 152A often heavily suffused with between 187B and 187C. The shoots bear few small prickles of similar shape and coloration.

I claim:

1. A new and distinct Climbing rose plant of the variety substantially as described and illustrated herein.

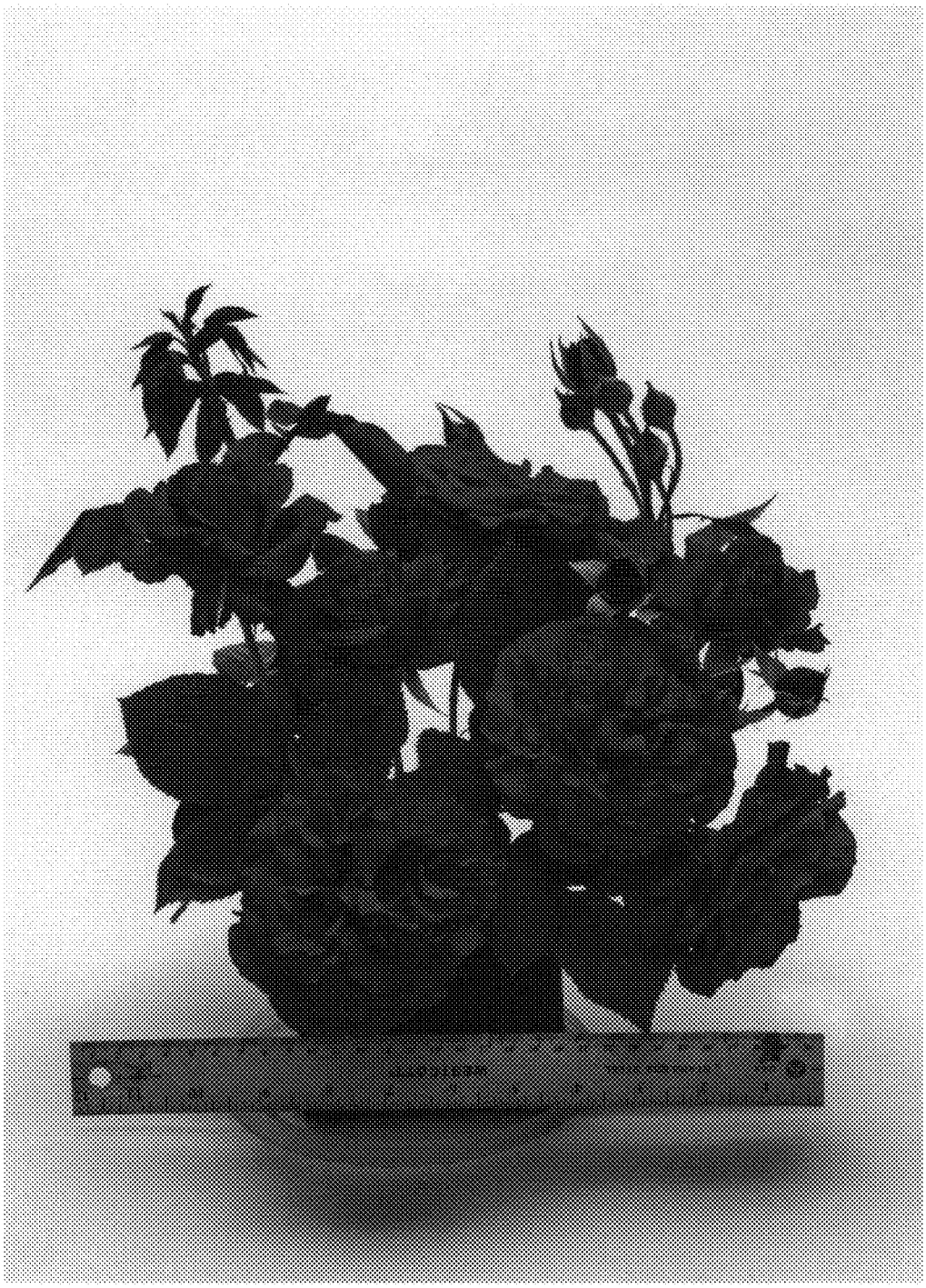

* * * * *